United States Patent
Vigneron et al.

(10) Patent No.: US 12,291,750 B2
(45) Date of Patent: May 6, 2025

(54) PREDICTIVE AND PROGNOSTIC USE OF A miRNA FOR HIGH GRADE SEROUS OVARIAN CARCINOMA THERAPEUTIC CARE

(71) Applicants: UNIVERSITE DE CAEN NORMANDIE, Caen (FR); INSTITUT NATIONAL DE LA SANTE ET DE LA RECHERCHE MEDICALE, Paris (FR); CENTRE REGIONAL FRANCOIS BACLESSE, Caen (FR); UNIVERSITE GRENOBLE ALPES, Saint Martin d'Heres (FR)

(72) Inventors: Nicolas Vigneron, Douvres la Delivrande (FR); Christophe Denoyelle, Saint-Germain-sous-Cailly (FR); Laurent Poulain, Thue et Mue (FR); Jean-Paul Issartel, Saint-Egreve (FR); Bernard Lambert, Cabourg (FR); Matthieu Meryet-Figuiere, Caen (FR); Mégane Vernon, Caen (FR); Audrey Guttin, Saint-Martin-le-Vinoux (FR)

(73) Assignees: UNIVERSITE DE CAEN NORMANDIE, Caen (FR); INSTITUT NATIONAL DE LA SANTE ET DE LA RECHERCHE MEDICALE, Paris (FR); CENTRE REGIONAL FRANCOIS BACLESSE, Caen (FR); UNIVERSITE GRNOBLE ALPES, Saint-Martin d'Héres (FR)

( * ) Notice: Subject to any disclaimer, the term of this patent is extended or adjusted under 35 U.S.C. 154(b) by 169 days.

(21) Appl. No.: 17/253,363

(22) PCT Filed: Jul. 4, 2019

(86) PCT No.: PCT/EP2019/068009
§ 371 (c)(1),
(2) Date: Dec. 17, 2020

(87) PCT Pub. No.: WO2020/007988
PCT Pub. Date: Jan. 9, 2020

(65) Prior Publication Data
US 2021/0269883 A1    Sep. 2, 2021

(30) Foreign Application Priority Data

Jul. 5, 2018   (EP) ..................... 18305887
Nov. 8, 2018   (EP) ..................... 18290130

(51) Int. Cl.
C12Q 1/68      (2018.01)
C12Q 1/6886    (2018.01)

(52) U.S. Cl.
CPC ..... *C12Q 1/6886* (2013.01); *C12Q 2600/106* (2013.01); *C12Q 2600/178* (2013.01)

(58) Field of Classification Search
None
See application file for complete search history.

(56) References Cited

U.S. PATENT DOCUMENTS

2011/0275534 A1* 11/2011 Cohn ................... C12N 15/113
                                                         435/6.12

FOREIGN PATENT DOCUMENTS

WO    2013/056217 A1    4/2013

OTHER PUBLICATIONS

Choi et al; Cell Reports, vol. 14, pp. 429-435; 2016.*
Vigneron et al; Molecular Oncology, vol. 10, pp. 981-992; 2016.*
The International Bureau of WIPO, International Preliminary Report on Patentability issued in International Application No. PCT/EP2019/068009, Jan. 5, 2021, 7 pages.
Choi, Y.E., et al., "Platinum and PARP Inhibitor Resistance Due to Over-Expression of MicroRNA-622 in BRCA1-Mutant Ovarian Cancer," Cell Rep 14(3):429-439, Jan. 26, 2016.
International Search Report mailed Oct. 4, 2019, issued in corresponding International Patent Application No. PCT/EP2019/068009, filed Jul. 4, 2019, 5 pages.
Kim, Y-W., et al., "Differential MicroRNA Expression Signatures and Cell Type-Specific Association With Taxol Resistance in Ovarian Cancer Cells," Drug Design, Development and Therapy 8:293-314, 2014.
Mandilaras, V., et al., "Updates and Current Challenges in MicroRNA Research for Personalized Medicine in Ovarian Cancer," Expert Opinion on Biological Therapy 17(8):927-943, 2017.
Vigneron, N., et al., "Towards a New Standardized Method for Circulating miRNAs Profiling in Clinical Studies: Interest of the Exogenous Normalization to Improve miRNA Signature Accuracy," Molecular Oncology 10(7):981-992, Apr. 2016.
Written Opinion mailed Oct. 4, 2019, issued in corresponding International Patent Application No. PCT/EP2019/068009, filed Jul. 4, 2019, 6 pages.

* cited by examiner

*Primary Examiner* — Jehanne S Sitton
(74) *Attorney, Agent, or Firm* — Christensen O'Connor Johnson Kindness PLLC

(57) ABSTRACT

The present disclosure relates to the identification of a biomarker, consisting in a circulating miRNA, suitable for use in the diagnosis and prognosis of high-grade serous ovarian carcinoma (HGSOC), and to diagnostic kits for use in such diagnosis.

Figure 1:
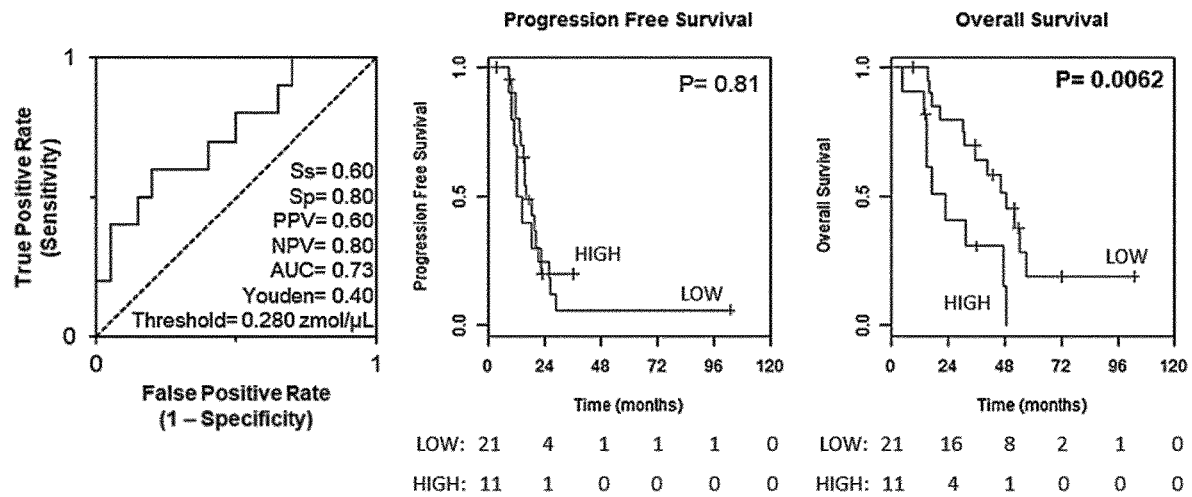

4 Claims, 5 Drawing Sheets
Specification includes a Sequence Listing.

PREDICTIVE AND PROGNOSTIC USE OF A miRNA FOR HIGH GRADE SEROUS OVARIAN CARCINOMA THERAPEUTIC CARE

The present invention relates to the identification of a biomarker, consisting in a circulating miRNA, suitable for use in the diagnosis and prognosis of high-grade serous ovarian carcinoma (HGSOC), and to diagnostic kits for use in such diagnosis.

Diagnostic and prognostic assays are standard tools for use by medical professionals and laypersons for the determination of a physiological change in a body cells or tissues which are indicative of a change in health status.

The yet unpredictable recurrence occurring in more than 75% of HGSOC patients, associated with the fact that the recurrent disease generally becomes unresponsive to conventional platinum-based chemotherapy, is responsible for the poor 5-year survival rate (<30% for stages III-IV). This situation is however expected to improve with time given the progressive emergence of targeted therapy. The use of PARP inhibitors (PARPi) as particularly effective agents in a specific molecular context [Homologous Repair Deficiency (HRD) phenotype] is a step in this direction. However, the improvement of HGSOC therapeutic management requires the identification and the validation of more reliable predictive and follow-up biomarkers, which remains at this time a major issue.

For time being, in order to make a definitive diagnosis of ovarian cancer, a gynecologic oncologist must perform surgery to gather samples for analysis by a pathologist. During the surgery, the surgeon will assess how far the disease has spread. This assessment is called "staging." Along with grading, these assessments help the oncologist recommend a treatment plan.

Staging in ovarian cancer has been standardized by the International Federation of Gynecology and Obstetrics (FIGO). While other factors impact prognosis, FIGO stage (there are four main stages, I to IV, see above) is by far the most important predictor of long term survival.

In Stage I ovarian cancer, cancer cells are found in one or both ovaries. Cancer cells may be found on the surface of the ovaries or in fluid collected from the abdomen (ascites). At this stage, cancer cells have not spread to other organs and tissues in the abdomen or pelvis, lymph nodes, or to distant sites:
 IA—Limited development in either one ovary or fallopian tube, where the outer ovarian capsule is not ruptured. There is no tumor on the external surface of the ovary and there is no ascites and/or the washings are negative.
 IB—Cancer is present in both ovaries or fallopian tubes, but the outer capsule is intact and there is no tumor on external surface. There is no ascites and the washings are negative.
 IC—The cancer is either Stage IA or IB level but the capsule is ruptured or there is tumor on the ovarian surface or malignant cells are present in ascites or washings.

In Stage II ovarian cancer, cancer cells have spread from one or both ovaries to other tissues in the pelvis. Cancer cells are found on the fallopian tubes, the uterus, the bladder, the sigmoid colon, or rectum in the pelvis. Cancer cells may be found in fluid collected from the abdomen:
 IIA—Extension or implants onto the uterus and/or fallopian tube. The washings are negative washings and there is no ascites.
 IIB—Extension or implants onto other pelvic tissues. The washings are negative and there is no ascites.
 IIC—Pelvic extension or implants like Stage IIA or IIB but with positive pelvic washings.

In Stage III ovarian cancer, cancer cells have spread to tissues outside the pelvis or to regional lymph nodes in the back of the abdomen (retroperitoneal lymph nodes). Cancer cells may be found on the outside of the liver:
 IIIA—Tumor is largely confined to the pelvis but with micro-scopic peritoneal metastases beyond pelvis to abdominal peritoneal surfaces or the omentum.
 IIIB—Same as IIIA but with macro-scopic peritoneal or omental metastases beyond pelvis less than 2 cm in size
 IIIC—Same as IIIA but with peritoneal or omental metastases beyond pelvis, larger than 2 cm or lymph node metastases to inguinal, pelvic, or para-aortic areas. Cancer may have also spread to the lymph nodes, but it has not spread to the inside of the liver or spleen or to distant sites.

In Stage IV ovarian cancer, the cancer cells have spread to tissues outside the abdomen and pelvis. Cancer cells may be found inside the spleen, the liver, in the lungs and in other organs located outside the peritoneal cavity:
 Stage IVA: Cancer cells are found in the fluid around the lungs (this is called a malignant pleural effusion) with no other areas of cancer spread outside the pelvis or peritoneal cavity.
 Stage IVB: Cancer has spread to the inside of the spleen or liver, to lymph nodes besides the retroperitoneal lymph nodes, and/or to other organs or tissues outside the peritoneal cavity. This includes the lungs, the brain, and the skin.

By looking at the cells in the tissue and fluid under a microscope, a pathologist describes the cancer as Grade 1, 2, or 3 (according to several cellular and histological features). Grade 1 is most like ovarian tissue and less likely to spread; Grade (2 and specially grade 3) cells are more irregular and more likely to metastasize. However, ovarian cancers are usually categorized as "low grade" (grade 1) or "high grade" (grade 2 or 3). High Grade Serous Ovarian Cancer (HGSOC) thus concerns patients having grade 2 or 3 and stage I to IV and ovarian cancer (Kurman R J. Origin and molecular pathogenesis of ovarian high-grade serous carcinoma. Ann Oncol. 2013 December; 24 Suppl 10:x16-21).

Several studies have been published on circulating miRNAs in the context of ovarian carcinoma; however, so far no miRNA has been introduced in the clinics as biomarker for such cancer, even if other known biomarkers currently used for diagnosis such as CA-125 and protein biomarkers (HE4) have limited prognosis value.

The goal of the studies conducted by the Inventors was thus to determine if the presence of circulating miRNAs from HGSOC patients can serve as non-invasive diagnostic and prognosis biomarkers of disease and therapy monitoring.

MicroRNAs (miRNAs) are small (19-25 nucleotides) non-coding regulatory RNAs that control protein expression at the post-transcriptional level through various mechanisms. About 2654 mature microRNAs (miRNAs) have been identified in the human genome (miRBase Release 22, March 2018, www.mirbase.org), and more than half of all human genes are believed to be regulated by miRNAs. As a single miRNA can regulate entire networks of genes, these molecules are considered the master regulators of the genome. Dysregulation of miRNAs can change or alter tumor suppressor proteins or activate oncogenes. Previous studies have shown that circulating miRNA could be utilized as a tool to gain a better understanding of both benign and malignant tumor conditions and for diagnosis purpose (Sourvinou et al., Quantification of circulating miRNAs in plasma: effect of preanalytical and analytical parameters on their isolation and stability, J Mol Diagn. 2013, 15 (6): 827-34).

Surprisingly, the Inventors have observed that one circulating miRNA (called hsa-miR-622 according to the nomenclature from miRBase) constitute an integrative signature and allows an effective prediction of the response to standard platinum-based chemotherapy and to innovative treatments such as PARPi.

Furthermore, specific modifications of said circulating miRNA profile, that occur after treatment in a response correlated manner, constitute follow-up tools useful for early detection of recurrence.

For clinicians, the identification of such molecular tools allows the identification of the patients that could be directed towards a platinum-based conventional chemotherapy or a specific strategy (such as PARPi, which have been recently introduced in clinical trials for the treatment of platinum-sensitive patients), to avoid unnecessary exposure to ineffective treatments with toxic or side effects, and the correct assessment of the early response to treatment as well as the follow-up of the pathology.

The present invention results from the studies of the expression of miRs by individual RT-qPCR assays in two independent homogenous cohorts, a retrospective cohort called "CRB" and a multicenter prospective cohort called "miRSA".

In summary, the results of these studies in HGSOC patients with advanced stages, have proved the interest of hsa-miR-622 circulating miRNA to predict both patient's responses to treatment:
  disease relapse (PFS, progression-Free Survival), and overall survival (OS).

This miRNA of interest can be used in clinical routine, using absolute dosages by RT-qPCR using exogenous normalizers and this methodology can be used for other biological fluids than blood (such as urine, ascites . . . ).

The definition of such circulating miRNA signature allows the guidance of the therapeutic decision allowing an orientation of patients predicted as being platinum- or PARPi-resistant towards alternative strategies and/or at least allows a better surveillance of patients with higher risk of recurrence. This prognosis is rendered easy thanks to a companion test (simple, cheap, fast and easily transposable in routine clinical use) to identify the platinum- or PARPi resistant patients in a timeframe compatible with therapeutic decisions.

The expression of hsa-miR-622 in tumor was previously associated with the resistance of HGSOC patients treated by platinum (Choi et al., Platinum and PARP Inhibitor Resistance Due to Overexpression of MicroRNA-622 in BRCA1-Mutant Ovarian Cancer, Cell Reports. 2016, 14 (3): 429-439), however the presence and the predictive relevancy of this miR were never investigated in the biofluids such as blood.

This invention thus relates to the definition of a circulating miRNA associated with prognosis in high-grade serous ovarian carcinoma (HGSOC). More particularly, this invention relates to determining the expression level of hsa-miR-622 in a biological sample (biofluids such as urine, ascite, blood, plasma, serum . . . ) from a patient using a simple, fast, economic and reliable test based on RT-qPCR.

According to a first aspect, the present invention relates to a method for the prognosis of the response of a HGSOC patient with advanced stages (III-IV) to a conventional platinum-based chemotherapy treatment comprising the steps of:
  determining at least the concentration of hsa-miR-622 in a liquid biological sample, preferably, blood, serum or plasma, of said HGSOC patient;
  comparing the obtained value with at least one reference value;
  and consequently determining if said patient is predicted as a platinum-sensitive patient or a platinum-resistant patient.

In the invention, the above method is preferably carried out before the administration of a conventional chemotherapy treatment to the HGSOC patient.

By "microRNA", "miRNA", or "miR" is meant a small (19-24 nt), non-protein-coding, endogenous RNA molecule. miRNA genes are estimated to account up to 2-5% of human genes and regulate 50% of coding genes. Loci that are responsible for miRNA expressions are located within introns of protein-coding or non-coding genes, in exons of non-coding genes, or in 3' UTRs. miRNAs have been shown to regulate mRNA expression and prevent protein production through the RNAi (RNA interference) pathway. A searchable database of published miRNA sequences and annotation is also available on the internet. Each entry in the miRBase Sequence database represents a predicted hairpin portion of a miRNA transcript (termed mir in the database), with information on the location and sequence of the mature miRNA sequence (termed miR). Both hairpin and mature sequences are available for searching and browsing, and entries can also be retrieved by name, keyword, references and annotation. All sequence and annotation data are also available for download. At present, the miRBase is hosted and maintained in the Faculty of Life Sciences at the University of Manchester, and was previously hosted and supported by the Wellcome Trust Sanger Institute.

The sequence of the target mature miRNA hsa-miR-622 (also designated miR-622) considered in the present invention is:
  ACAGUCUGCUGAGGUUGGAGC (SEQ. ID. N° 1).

In an embodiment, the method of the invention can be carried out by determining the concentration of an "iso-miR" of hsa-mir-622. Such an iso-miR differs from the miR by a few nucleotides (Bartel D. P., Metazoan MicroRNAs, Cell. 2018, 173 (1): 20-51). For example, the sequence of an "iso-miR of hsa-miR-622" can differ from 1 to 5 nucleotides in comparison to the sequence SEQ ID NO: 1.

In another embodiment, the method of the invention can be carried out by determining the concentration of the "hsa-pre-miR-622", which corresponds to the precursor RNA of hsa-mir-622. The sequence of the hsa-pre-miR-622 is:

(SEQ ID NO: 2)
AGAGAAGCUGGACAAGUACUGGUCUCAGCAGAUUGAGGAGAGCACCACA
GUGGUCAUCACACAGUCUGCUGAGGUUGGAGCUGCUGAGAUGACACU.

In the invention, the expressions "conventional platinum-based chemotherapy treatment" or "conventional chemotherapy treatment" refer to a first-line platinum-based therapy, preferably with Carboplatin either or not in combination with Paclitaxel, more preferably with Carboplatin and Paclitaxel used in combination.

For the evaluation of a diagnostic test, predictive values help interpreting the results of tests in the clinical setting. The diagnostic value of a procedure is defined by its sensitivity, specificity, predictive value and efficiency. Any test method will produce True Positive (TP), False Negative (FN), False Positive (FP), and True Negative (TN).

The "sensitivity" of a test is the percentage of all patients with disease present or that do respond who have a positive test or TP/(TP+FN)×100%.

The "specificity" of a test is the percentage of all patients without disease or who do not respond, who have a negative test or TN/(FP+TN)×100%.

The "predictive value" or "PV" of a test is a measure (%) of the times that the value (positive or negative) is the true value, i.e., the percent of all positive tests that are true positives is the Positive Predictive Value (PV+) or TP/(TP+FP)×100%. The "negative predictive value" (PV) is the percentage of patients with a negative test who will not respond or TN/(FN+TN)×100%.

The "accuracy" or "efficiency" of a test is the percentage of the times that the test give the correct answer compared to the total number of tests or (TP+TN)/(TP+TN+FP+FN)×100%. The "error rate" calculates from those patients predicted to respond who did not and those patients who responded that were not predicted to respond or (FP+FN)/(TP+TN+FP+FN)×100%. The overall test "specificity" is a measure of the accuracy of the sensitivity and specificity of a test do not change as the overall likelihood of disease changes in a population, the predictive value does change. The PV changes with a physician's clinical assessment of the presence or absence of disease or presence or absence of clinical response in a given patient.

Hsa-miR-622 is an endogenous miRNA which is expressed in ovarian cancer cells and in the serum of ovarian cancer patients.

As shown for the first time by the Inventors, circulating hsa-miR-622 expression allows to classify HGSOC patients as being at high- or low-risk of relapse and is also a strong predictor of overall survival.

Moreover, using multivariates analyses, the Inventors have shown that circulating hsa-miR-622 expression maintains its prognostic effect when adjusted for relevant clinical covariates, such as tumor stages and residual disease after primary surgery.

Thus, the comparison of the value of the concentration of hsa-miR-622 in biofluid to a reference value allows to differentiate HGSOC patients into low-risk or high-risk groups in terms of cancer recurrence (PFS) and overall survival (OS).

Practically, from their circulating hsa-miR-622 profile, HGSOC patients can be predicted either as platinum-resistant patients or as platinum-sensitive patients.

According to the invention, a "platinum-resistant patient" (or "early relapser") refers to a HGSOC patient who relapses less than six months after the end of the platinum-based first-line chemotherapy. In most cases, platinum-resistant patients are short-term survivors, with an overall survival inferior to 24 months.

At the opposite, a "platinum-sensitive patient" (or "late relapser") refers to a HGSOC patient who does not relapse or who relapses more than six months after the end of the platinum-based first-line chemotherapy (i.e. platinum-sensitive relapsed patient). In most cases, platinum-sensitive patients are long-term survivors, with an overall survival of at least 24 months.

In an embodiment, the hsa-miR-622 concentration can be used at baseline to predict the treatment response irrespective of treatment sequence (PDS or NACT), before decision making, in particular, if the value of the circulating hsa-miR-622 concentration is strictly lower than 0.128 zmol/µl, the tested patient can be predicted as a platinum-sensitive patient, in particular, if the value of the circulating hsa-miR-622 concentration is equal to or higher than 0.128 zmol/µl, the tested patient can be predicted as a platinum-resistant patient.

In another embodiment, the hsa-miR-622 concentration can be used at baseline to predict the treatment response in combination with treatment sequence (PDS or NACT), after decision making:

in particular, if the value of the circulating hsa-miR-622 concentration is strictly lower than 0.124 zmol/µl, the tested patient can be predicted as a platinum-sensitive patient, in particular, if the value of the circulating hsa-miR-622 concentration is equal to 0.28 zmol/µl or higher, the tested patient can be predicted as a platinum-resistant patient, in particular, if the value of the circulating hsa-miR-622 concentration is equal to or higher than 0.124 zmol/µl and strictly lower than 0.28 zmol/µl, the tested patient can be predicted as:

a platinum-resistant patient if she is treated with neoadjuvant chemotherapy, or a platinum-sensitive patient if she is treated with a primary debulking surgery instead of neoadjuvant chemotherapy.

In the invention, the term "neoadjuvant chemotherapy" (or NACT) refers to a drug treatment that takes place before surgical extraction of a tumor and/or before the administration of the main treatment of the cancer.

In another embodiment, the hsa-miR-622 concentration can be used to predict the treatment response at relapse:

in particular, if the patient is in relapse and if the value of the circulating hsa-miR-622 concentration is lower than 0.34 zmol/µl, the tested patient can be predicted as a platinum-sensitive patient, in particular, if the patient is in relapse and if the value of the circulating hsa-miR-622 concentration is equal to 0.34 zmol/µl or higher, the tested patient can be predicted as a platinum-resistant patient.

In particular, the circulating hsa-miR-622 concentration can be determined by a RT-qPCR, a microarray or a next generation sequencing (NGS).

More particularly, the circulating hsa-miR-622 concentration can be determined by a TaqMan™ RT-qPCR.

For example, from a sample of biofluid (preferably serum or plasma) sampled before the first-line chemotherapy, total RNA are isolated using the NucleoSpin® miRNA plasma kit (Macherey-Nagel), even other kits could be employed. Then an aliquot of the total RNA solution is retro transcribed, for example using the TaqMan™ reverse transcription kit, and then amplified, for example with TaqMan™ chemistry.

In particular, absolute dosages of the circulating hsa-miR-622 concentration can be achieved first by assaying the hsa-miR-622 amount in the sample by comparison with miRNAs standard curves obtained by measurement of known amount of synthetic hsa-miR-622 oligonucleotides and second by using an exogenous normalization based on the addition of known quantities of cel-miR-39-3p, cel-miR-54-3p and cel-miR-238-3p in the biofluid just before the RNA extraction step so that absolute quantitation in the biofluid can be calculated as previously described [Vigneron et al., Towards a new standardized method for circulating miRNAs profiling in clinical studies: Interest of the exogenous normalization to improve miRNA signature accuracy, Mol Oncol. 2016, 10 (7): 981-92]. Depending of the methods used for RNA extraction, the value of the circulating hsa-miR-622 concentration can vary, for example from 5% to 10%.

In an embodiment, the liquid biological sample is selected among urine, blood, serum, plasma, ascites, preferably it is serum.

The method of the invention can be carried out ex vivo or in vitro.

All the features and embodiments disclosed herein for the above method can be transposed mutatis mutandis to the following methods according to the invention.

In another aspect, the present invention relates to a method for monitoring the sensitivity of a HGSOC patient to a conventional platinum-based chemotherapy treatment comprising the steps of:
- determining at least the concentration of hsa-miR-622 in a liquid biological sample of said HGSOC patient wherein said liquid biological sample is obtained during the conventional platinum-based chemotherapy treatment;
- comparing the obtained value with at least one reference value;
- determining if said patient is sensitive or not to said conventional platinum-based chemotherapy treatment. The methods of the invention can also be used to determine if a treatment failure in a patient is correlated to a modification of the platinum resistance of the tumor.

The methods of the invention can also be used to detect a tumor escapement.

In another aspect, the invention also relates to a method of diagnosis and treatment of HGSOC in a patient, said method comprising:
- obtaining a liquid biological sample from a human patient suffering from HGSOC;
- determining the concentration of hsa-miR-622 in the liquid biological sample of said patient;
- diagnosing the patient as a platinum-sensitive patient or a platinum-resistant patient by comparison of the concentration of hsa-miR-622 with at least one reference value;
- administering a conventional platinum-based chemotherapy treatment and/or a PARPi treatment to the diagnosed platinum-sensitive patient.

The present invention further relates to a test kit for use in the methods of the present invention comprising at least: one oligonucleotide probe capable of binding to at least a portion of circulating hsa-miR-622.

In an embodiment, the kit of the invention is a PCR kit.

In an embodiment, the test kit of the invention further contains at least one reference RNA and/or at least one specific oligonucleotide probe capable of binding to at least a portion of said reference RNA.

Said reference RNA can be used to produce absolute standard curves to determine the absolute concentration of hsa-miR-622 in the biological sample.

Said reference RNA is preferably absent in the biological sample. For example, said reference RNA can be cel-miR-54-3p (UACCCGUAAUCUUCAUAAUCCGAG, SEQ ID NO: 3) or cel-miR-238-3p (UUUGUACUCCGAUGC-CAUUCAGA, SEQ ID NO: 4, which correspond to two miRs expressed in the biological model *Caenorhabditis elegans*.

Preferably, said RNA reference is a synthetic RNA.

The kit may be adapted for performance of an assay selected from a real-time PCR assay. Other technologies such as miRNA microarrays as well as NGS (next generation sequencing) may be also used to quantify miRNA expression.

In an embodiment, the kit of the invention further contains primers which allow testing of RNA isolation yield controls.

In another aspect, the invention provides the use of the concentration of hsa-miR-622 measured in a liquid biological sample, preferably blood, serum or plasma, as a biomarker to stratify HGSOC patients according to expected prognosis and/or to expected response to a conventional platinum-based chemotherapy treatment.

In another aspect, the invention provides the use of the concentration of hsa-miR-622 measured in a liquid biological sample, preferably blood, serum or plasma, as a biomarker to stratify HGSOC patients according to expected prognosis and/or to expected response to a PARPi treatment.

In the present invention, the expression "PARPi treatment" refers to the administration to the patient of at least one chemical compound that acts as a pharmacological inhibitor of an enzyme of the PARP (poly ADP ribose polymerase) family, in particular PARP-1. A PARP inhibitor can be selected from, but no limited to, the group comprising Olaparib, Niraparib, Talazoparib, Veliparib, Pamiparib, Rucaparib, CEP 9722, E7016, Iniparib and 3-aminobenzamide.

Indeed, it has been shown that responses to a treatment with PARP inhibitors are associated with platinum-sensitivity. In particular, it is admitted that platinum-sensitivity can be considered as a clinical biomarker to identify patients more likely to be sensitive to PARPi (de Picciotto et al., Ovarian cancer: Status of homologous recombination pathway as a predictor of drug response, Crit Rev Oncol Hematol. 2016, 101:50-59; Choi et al., Platinum and PARP Inhibitor Resistance Due to Overexpression of MicroRNA-622 in BRCA1-Mutant Ovarian Cancer, Cell Reports. 2016, 14 (3): 429-439). This similarity between the response to Platinum-based treatment and PARPi-based treatment was validated in the present invention as shown in the Examples (see Example VIII).

For this reason, the features and embodiments of the invention using the concentration of hsa-miR-622 measured in a liquid biological sample as a biomarker for the platinum sensitivity/resistance apply mutatis mutandis to the invention using the concentration of hsa-miR-622 measured in a liquid biological sample as a biomarker for PARPi sensitivity/resistance.

Thus, the invention also provides a method for the prognosis of the response of a HGSOC patient with advanced stages to a PARPi-based treatment comprising the steps of:
- determining at least the concentration of hsa-miR-622 in a liquid biological sample of said HGSOC patient;
- comparing the obtained value with at least one reference value;
- and consequently determining if said patient is predicted as a PARPi-sensitive patient or a PARPi-resistant patient.

In an embodiment, the hsa-miR-622 concentration can be used at baseline to predict the treatment response irrespective of treatment sequence (PDS or NACT), before decision making:

in particular, if the value of the circulating hsa-miR-622 concentration is strictly lower than 0.128 zmol/µl, the tested patient can be predicted as a PARPi-sensitive patient, in particular, if the value of the circulating hsa-miR-622 concentration is equal to or higher than 0.128 zmol/µl, the tested patient can be predicted as a PARPi-resistant patient.

In another embodiment, the hsa-miR-622 concentration can be used at baseline to predict the treatment response in combination with treatment sequence (PDS or NACT), after decision making:

in particular, if the value of the circulating hsa-miR-622 concentration is strictly lower than 0.124 zmol/µl, the tested patient can be predicted as a PARPi-sensitive patient, in particular, if the value of the circulating hsa-miR-622 concentration is equal to 0.28 zmol/µl or higher, the tested patient can be predicted as a PARPi-resistant patient, in particular, if the value of the circulating hsa-miR-622 concentration is equal to or higher than 0.124 zmol/µl and strictly lower than 0.28 zmol/µl, the tested patient can be predicted as:

a PARPi-resistant patient if she is treated with neoadjuvant chemotherapy, or a PARPi-sensitive patient if she is treated with a primary debulking surgery instead of neoadjuvant chemotherapy.

In another embodiment, the hsa-miR-622 concentration can be used to predict the treatment response at relapse:

in particular, if the patient is in relapse and if the value of the circulating hsa-miR-622 concentration is lower than 0.34 zmol/µl, the tested patient can be predicted as a PARPi-sensitive patient, in particular, if the patient is in relapse and if the value of the circulating hsa-miR-622 concentration is equal to 0.34 zmol/µl or higher, the tested patient can be predicted as a PARPi-resistant patient.

In another aspect, the invention also provides the use of the concentration of hsa-miR-622 measured in a liquid biological sample, preferably blood, serum or plasma, as a biomarker for the early detection of a relapse of HGSOC patients.

In an embodiment, a relapse can be detected by monitoring the evolution of the concentration of hsa-miR-622 measured in the liquid biological sample by multiple analyses made at regular intervals, for example once year, every six months or every three months.

In an embodiment, the emergence of a resistance to a platinum-based chemotherapy or to a PARPi-based treatment can be detected by monitoring the evolution of the concentration of hsa-miR-622 measured in the liquid biological sample by multiple analyses made at regular intervals, for example once year, every six months or every three months.

FIGURES

FIG. 1. Progression-free survival and Overall survival stratified by risk according to serum hsa-miR-622 expression in CRB cohort. Hsa-miR-622 high-risk and low-risk curves were compared with the log-rank test. Ss: sensitivity; Sp: specificity; PPV: Positive Predictive Value; NPV: Negative Predictive Value; AUC: Area Under Curve, P: p-values.

Figure 2:
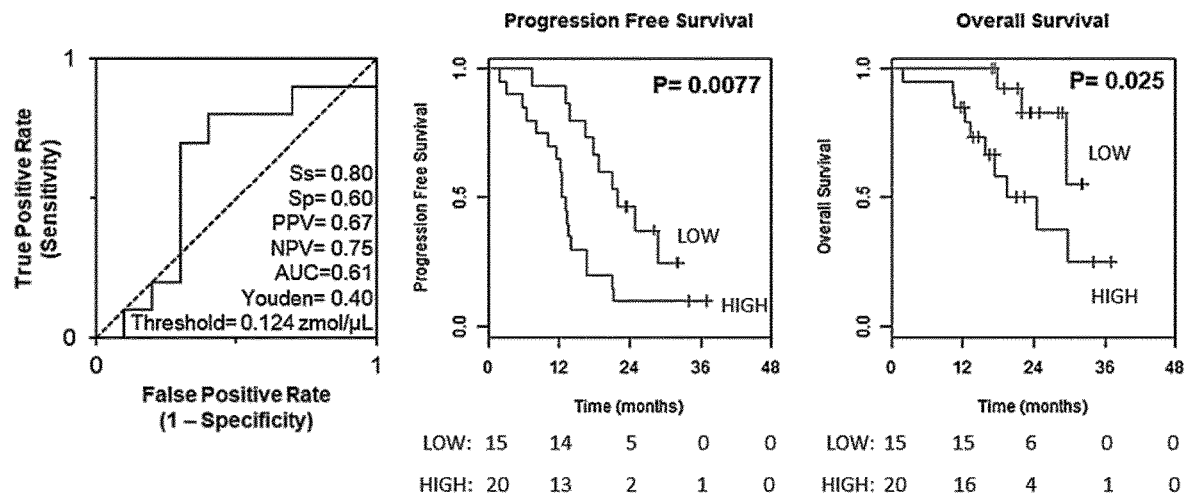

FIG. 2. Progression-free survival and Overall survival stratified by risk according to serum has-miR-622 expression in miRSA cohort. Hsa-miR-622 high-risk and low-risk curves were compared with the log-rank test. Ss: sensitivity; Sp: specificity; PPV: Positive Predictive Value; NPV: Negative Predictive Value; AUC: Area Under Curve, P: p-values.

Figure 3:
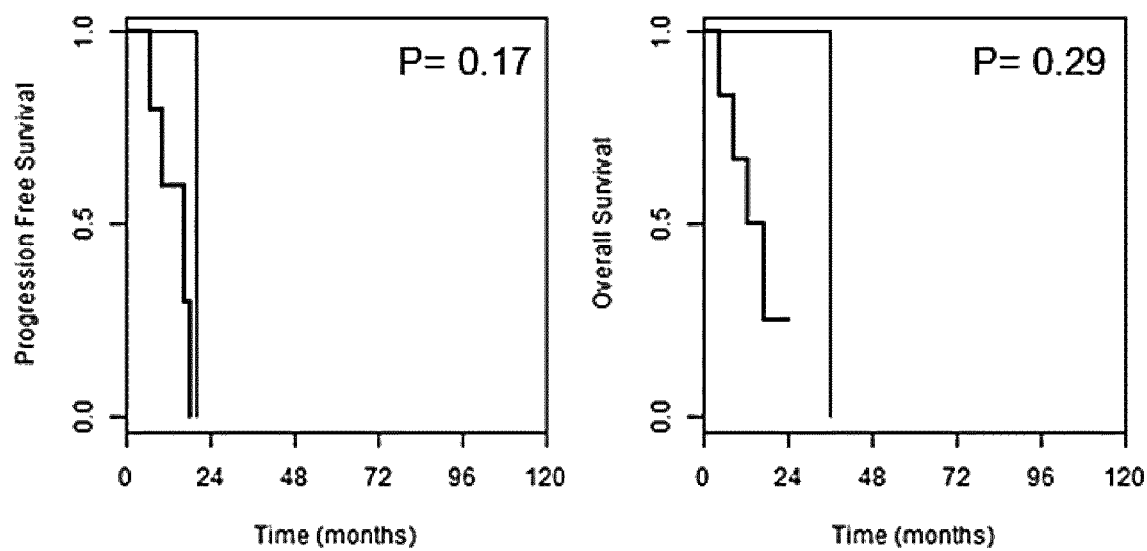

FIG. 3. Progression-free survival and Overall survival stratified by risk according to serum hsa-miR-622 expression in NACT patients of CRB cohort. Hsa-miR-622 high-risk (bold) and low-risk (thin) curves were compared with the log-rank test, P: p-values.

Figure 4:
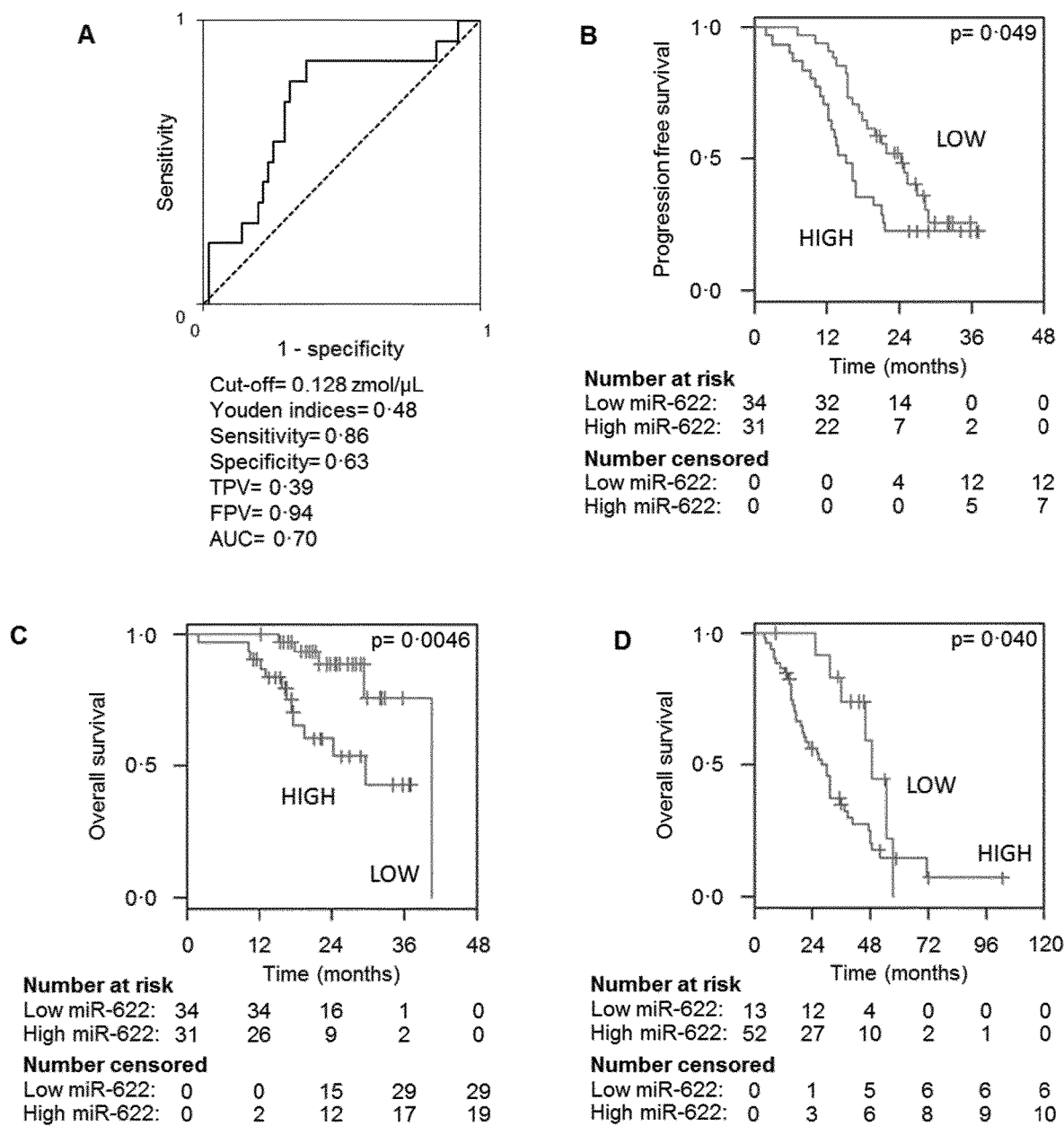

FIG. 4. MiRSA and CRB cohorts survivals stratified by baseline serous miR-622 expression.

Sorting miRSA patients into platinum-resistant (PFI<6 months) and platinum-sensitive (PFI≥6 months) relapses, a ROC curve provide a cut-off value of 0.128 zmol/µL based on the best Youden indices (A). Using the cut-off value of 0.128 zmol/µL on the baseline serous expression of hsa-miR-622, Kaplan-Meier curves show the stratification of progression-free survival and overall survival in the miRSA cohort (B & C) and the stratification of progression-free survival in the CRB cohort (D). Curves were compared using the log-rank test. ROC=Receiveir Operating Characteristic, TPV=True-Positive Value, FPV=False Positive Value, AUC=Area Under the Curve.

Figure 5:
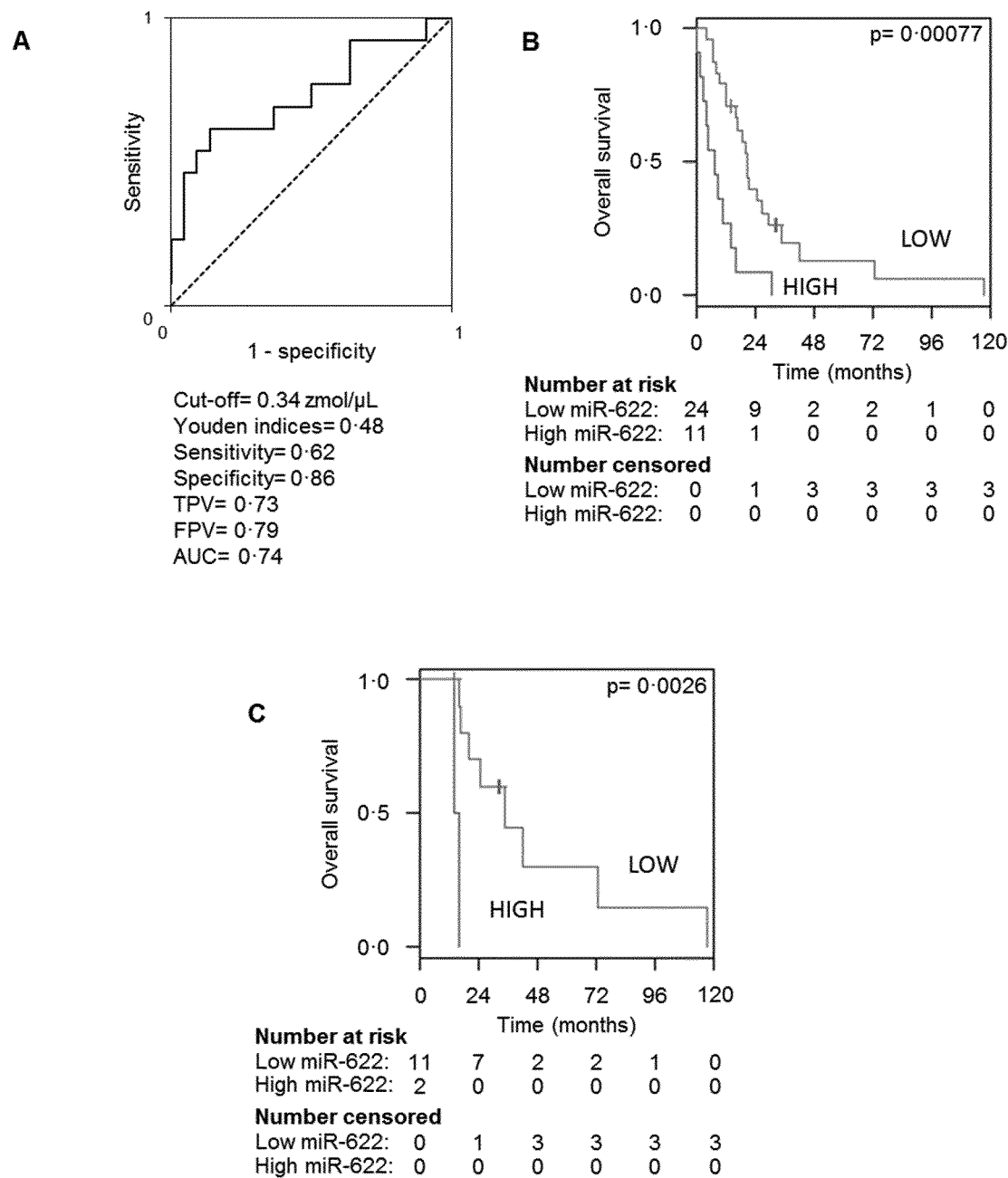

FIG. 5. CRB cohort overall survival stratified by relapse serous miR-622 expression. Sorting CRB patients into short (OS<12 months) and long (OS≥12 months) surviveirs from their relapses, a ROC curve provide a cut-off value of 0.34 zmol/µL based on the best Youden indices (A). Using the cut-off value of 0.34 zmol/µL on the serous expression of hsa-miR-622, Kaplan-Meier curves show the stratification of overall survival at relapse in the CRB cohort (B) and in CRB platinum-sensitive relapsers who respond to the second line platinum-based chemotherapy (C). Curves were compared using the log-rank test. ROC=Receiveir Operating Characteristic, TPV=True-Positive Value, FPV=False Positive Value, AUC=Area Under the Curve.

Figure 6:
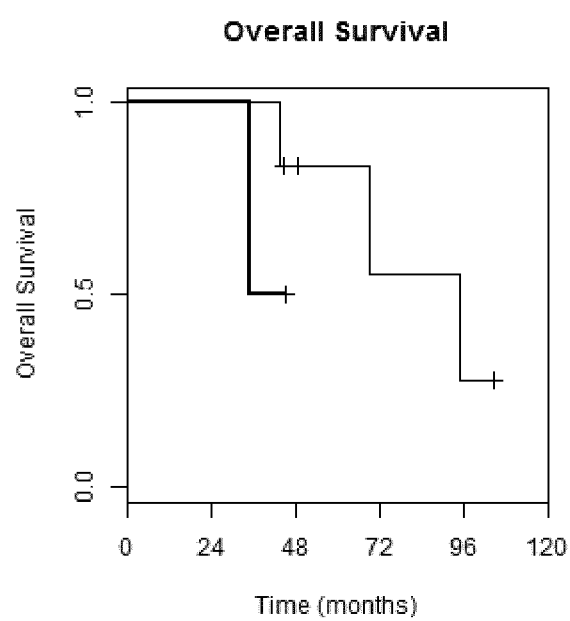

FIG. 6. Overall survival stratified by risk according to serum hsa-miR-622 expression in patients (CRB cohort) treated by PARPi-maintenance at progression. Hsa-miR-622 high-risk (bold) and low-risk (thin) curves were compared with the log-rank test.

EXAMPLES

Materials and Methods

Patient Blood Samples

In total, two treatment-naive cohorts of samples from women with HGSOC (stages III and IV) were used for this study: CRB (retrospective cohort) and miRSA (multicentric prospective cohort, NCT01391351). The cohorts were restricted to patients who met disease and treatment homogenous criteria whose clinical characteristics are summarized in Table 1.

TABLE 1

| Clinical characteristics of patients. | | | | | | |
|---|---|---|---|---|---|---|
| Cohorts | miRSA baseline | (n = 65) | CRB baseline | (n = 65) | CRB relapse | (n = 35) |
| Age (±SD) | 63.6 | (±9.3) | 64.7 | (±11.3) | 61.8 | (±9.7) |
| Histology | | | | | | |
| Serous | 65 | (100.0%) | 65 | (100.0%) | 35 | (100.0%) |
| Stages | | | | | | |
| III | 49 | (75.4%) | 48 | (73.8%) | 31 | (88.6%) |
| IV | 16 | (24.6%) | 17 | (26.2%) | 4 | (11.4%) |
| Grades | | | | | | |
| 2 | 17 | (26.2%) | 6 | (9.2%) | 6 | (17.1%) |
| 3 | 43 | (66.2%) | 59 | (90.8%) | 29 | (82.9%) |
| High | 5 | (7.7%) | 0 | (0.0%) | ) | (0.0%) |
| Primary surgery residues | | | | | | |
| Absence (R0) | 34 | (52.3%) | 20 | (30.8%) | 7 | (20.0%) |
| Microscopic (<10 mm) | 4 | (6.2%) | 20 | (30.8%) | 13 | (37.1%) |
| Macroscopic (≥10 mm) | 4 | (6.2%) | 23 | (35.4%) | 15 | (42.9%) |
| Biopsy | 23 | (35.4%) | 2 | (3.1%) | 0 | (0.0%) |
| Unknown | 0 | (0.0%) | 0 | (0.0%) | 0 | (0.0%) |
| Treatment sequence | | | | | | |
| PDS | 30 | (46.2%) | 58 | (89.2%) | 35 | (100.0%) |
| NACT | 35 | (53.8%) | 7 | (10.8%) | 0 | (0.0%) |
| Primary response | | | | | | |
| Complete response | 41 | (63.1%) | 32 | (49.2%) | 19 | (54.3%) |
| Partial response | 13 | (20.0%) | 27 | (41.5%) | 16 | (45.7%) |
| Stable Disease | 7 | (10.8%) | | | | |
| Progressive Disease | 3 | (4.6%) | 2 | (3.1%) | 0 | (0.0%) |
| Unknown | 1 | (1.5%) | 4 | (6.2%) | 0 | (0.0%) |
| Platinum sensitivity | | | | | | |
| Fully sensitive | 33 | (50.8%) | 21 | (32.3%) | 16 | (45.7%) |
| Partly sensitive | 18 | (27.7%) | 19 | (29.2%) | 10 | (28.6%) |
| Resistant | 11 | (16.9%) | 15 | (23.1%) | 7 | (20.0%) |
| Refractory | 3 | (4.6%) | 4 | (6.2%) | 1 | (2.9%) |
| Unknown | 0 | (0.0%) | 6 | (9.2%) | 1 | (2.9%) |
| PFS | 18.7 | [13.4-25.6] | | | | |
| OS | 21.0 | [16.6-27.5] | 31.2 | [15.9-45.8] | 16.0 | [8.2-25.9] |

Data are median ± quartiles for ages, PFS and OS or n (%) for other parameters.
PDS = Primary Debulking Surgery,
NACT = Neoadjuvant Chemotherapy.

Biological Resources Center (CRB) OvaRessources (Retrospective Cohort)

All the serum samples used retrospectively in this project were collected by the Department of Gynecologic Oncology at Comprehensive Cancer Center (CCC) F. Baclesse, Caen, France (since 2000) and came from the biobank of Biological Resources Center (CRB) OvaRessources (ISO 9001 quality management). The serum samples were stored at −20° C. in optimal conditions of quality and safety. All patients gave their written consent for the conservation in the biological collections of CCC F. Baclesse and their use in the context of a biological research. These serum samples were obtained in compliance with French regulations in force, particularly the provisions relating to biomedical research of the Public Health Code, and following the laws of bioethics, the Computer Law and Freedoms, the Helsinki Declaration, and Good Clinical Practice (GCP). In addition, they have been submitted in accordance with their respective regulations to the competent authorities, namely the ANSM (National Agency for the Safety of Medicines), the CPP (Committee for the Protection of Individuals), the ARH (Regional Agency for Hospitalization), the MESR (Ministry of Education, Health and Research) and the CNIL (National Commission for Computing and Freedoms).

The analyses shown in examples I and III were restricted on serum samples from 39 histologically verified clinically high grade serous ovarian carcinoma (stages III-IV). These serum samples were collected before surgery and before platinum based-chemotherapy for patients treated with primary debulking surgery (PDS, N=32) or with neoadjuvant chemotherapy (NACT, N=7).

The extended analyses shown in example V were done on 65 histologically verified clinically HGSOC for baseline samples.

The analyses shown in example VI were done on 35 histologically verified clinically HGSOC for relapse samples.

The analyses shown in example VII were done on 13 histologically verified clinically HGSOC eligible to PARPi (relapse beyond 6 months and response to platinum-based second line chemotherapy) for relapse samples.

The analyses shown in example VIII were done on serum samples from 8 histologically verified clinically HGSOC (CRB cohort). These serum samples were collected prior to first-line chemotherapy on patients treated by PARPi maintenance at progression.

miRSA (miRNA Serum Analysis) Cohort

Serum samples were obtained from patients who were included in miRSA clinical study between 2011 and 2013 (NCT01391351). MiRSA study was conducted by dedicated clinical teams and oncological laboratories, with the respect to standard operating procedures. This study was approved by the ethics committee "Nord-Ouest III" [CPP N° 2011 02] and national authorities (AFSSAPS N°B110260-20). Prior to scientific use of samples and data, patients were appropriately informed and asked to consent in writing, in compliance with French and European regulations. Patient's sera were collected on SST II tubes (BD Vacutainer®, Becton Dickinson, Le Pont de Claix, France) and processed according to a routine pre-analytical protocol. Briefly, biofluids were centrifuged twice to remove all residual cells and then were frozen immediately at −80° C. Experiments were done with RNAs thawed only once. RNAse-free protocols were followed throughout all the procedures.

The analyses shown in Example II were restricted on serum samples from 35 histologically verified clinically high grade serous ovarian carcinoma (stages III-IV) with enough serum for ancillary studies. These serum samples were collected before platinum based-chemotherapy for patients treated with neoadjuvant chemotherapy (NACT).

The extended analyses shown in example IV were done on 65 histologically verified clinically HGSOC for baseline samples.

Outcomes

The primary endpoint was progression-free survival (PFS) because the main goal of the predictor was to be able to identify patients at risk of early relapse. Progression-free survival was defined as the time (in months) between the date of diagnosis and the date of progression or death, whichever occurred first, or the date of last follow-up for patients alive without progression.

The secondary endpoint was overall survival (OS), which was defined as the time (in months) between the date of diagnosis and the date of death or the date of last contact for surviving patients.

Synthetic miRNAs

SDS-PAGE purified synthetic microRNAs was purchased from Eurogentec (Liège, Belgium) for hsa-miR-622 (SEQ ID NO: 1), cel-miR-54-3p (UACCCGUAAUCUU-CAUAAUCCGAG (SEQ ID NO: 3) and cel-miR-238-3p (UUUGUACUCCGAUGCCAUUCAGA, SEQ ID NO: 4). Oligonucleotides were stored at −80° C. at a concentration of 20 µM.

RNA Isolation from Serum Samples

MiRNAs were isolated from blood serum samples according to the manufacturers' recommendations and previous published methodology (Vigneron et al., 2016), using the commercially available NucleoSpin® miRNA Plasma kit (Macherey-Nagel, Hoerdt, France). After the denaturation step, 1500 attomoles of cel-miR-54-3p and cel-miR-238-3p synthetized by Eurogentec were added in each sample. Total RNAs were eluted in 30 µL with nuclease-free water and were then frozen at −80° C.

Absolute Quantification of miRNAs Using RT-qPCR

MiRNAs were first retro-transcribed using specific stem-loop primers (Thermo Fisher Scientific, Life Technologies) and MicroRNA Reverse Transcription Kit (Thermo Fisher Scientific, Life Technologies) before to be amplified with hydrolysis probes (Thermo Fisher Scientific, Life Technologies). Briefly, 5 µL of isolated RNA were mixed with 10 µL of RT master mix. Then, triplicates with 1.33 µL of cDNA were mixed with 18.7 µL of qPCR master mix (Universal Master Mix II without UNG) in 96-wells optical plates. The Thermo Fisher ID references for stem-loop primers and hydrolysis probes were the following: cel-miR-54-3p (001361), cel-miR-238-3p (000248) and hsa-miR-622 (001553). Fluorescence and threshold baselines were measured using an Applied ABI Prism 7500 Fast PCR system with the 7500 Software v2.0.6 (Thermo Fisher Scientific, Life Technologies, Applied Biosystems). Absolute standard curves were made by diluting synthetic cel-miR-54-3p, cel-miR-238-3p, and hsa-miR-622 at 2.105, 2.104, 2.103, 2.102, 2.101 and 2 zmol/µL prior to RT-qPCR steps. They were used to convert quantitative cycles (Cq) into miRNAs concentrations in attomole per microliter of RNA extracts. Serum isolation yields of cel-miR-54-3p and cel-miR-238-3p were calculated for each sample by dividing recovery quantities by added quantities and their geometric means were used to estimate hsa-miR-622 concentration in zeptomole per microliter of serum.

Statistical Analyses

Platinum-free interval (PFI) is defined as the interval from the last date of platinum-based first-line chemotherapy until progressive disease (relapse, death or lost to follow-up) is documented. Ovarian cancer patients were typically classified as being either platinum-resistant or platinum-sensitive relapsed (PFI<6 and ≥6 months, respectively).

Patients were also classed into short and long survivors (OS<24 and ≥24 months, respectively).

Using a ROC curve, for each cohort, hsa-miR-622 value threshold was selected according to the best Youden indices.

Patients were then classified according to their hsa-miR-622 expression into low and high expression groups. The hsa-miR-622 value threshold prognosis interest on PFS and OS was assessed with Kaplan-Meier curves, using Log Rank test and the Cox univariate and multivariate analyses with the sequential method. Surgery outcome (absence or presence of macroscopic residues) and stage (III or IV) were included in multivariate analyses as already known pre-chemotherapy prognosis factors.

Example I: Association of Serum Hsa-miR-622 Expression Levels and Overall Survival in PDS Patients of CRB Cohort Based on previous observation showing the prognostic interest of hsa-miR-622 in ovarian cancer tumors, its expression was analyzed in serum patients from CRB cohort. As previously, patients were classed in short and long survivors (<24 and ≥24 months, respectively) and best discriminant hsa-miR-622 value was identify according to the best Youden indice, using a ROC curve. Patients were separated in two groups of high and low hsa-miR-622 expression (cutoff=0.28 zmol/μL or 169 copies/μL). It was observed that high serum hsa-miR-622 expression group presents significant worse OS compared with low hsa-miR-622 expression group (median OS 22.8 versus 48.9 months, log rank p=0.0062) (see FIG. 1). No significant difference was observed for PFS between low and high hsa-miR-622 groups (p=0.81). Next, a Cox univariate model was used to estimate the hazard ratio (HR) for each relevant prognostic variable. High hsa-miR-622 expression group (HR=3.43, CI95% 1.3-8.7, p=0.0098) and suboptimum debulking after primary surgery (HR=3.41, CI95% 1.1-10.2, p=0.028) were significantly associated with OS in univariate analysis (see Table 2). A multivariate analysis with a Cox regression model was then used to assess the prognostic effect of hsa-miR-622 in the context of concomitant effects of other known prognostic factors (i.e., stage and residual disease). Unexpectedly, hsa-miR-622 maintained its independent prognostic effect (for OS, p=0.044) when analyzed in multivariate analysis adjusting for these clinical covariates.

the 10 short survivors with 60.0% of sensitivity, 80.0% of specificity, 60.0% of true predictive value and 80.0% of false predictive value.

Example II: Prognosis Interest of Serum Hsa-miR-622 Expression Levels in NACT Patients of miRSA Cohort The serum hsa-miR-622 expression level was analyzed in the patients samples from the miRSA cohort. Two groups of high and low hsa-miR-622 expression were constituted (cutoff=0.124 zmol/μL or 75 copies/μL). In good agreement with previous observations done on CRB cohort, high expression of serum hsa-miR-622 predicted a worse overall survival [24.4 versus ≥32.2 months (end survival probability >0.5); log rank p=0.025] (see FIG. 2). Interestingly, it was also found that high serum hsa-miR-622 expression group presents significant lower PFS in comparison to low hsa-miR-622 expression group (median PFS 12.7 versus 22 months, log rank p=0.0077). This miRNA signature could differentiate women treated for HGSOC into low-risk or high-risk groups in terms of cancer recurrence, with a difference in the median progression-free survival of 9.4 months between the high risk and low risk groups. Next, univariate and multivariate analyses of miRSA cohort were

TABLE 2

Univariate and Multivariate analyses of the serum hsa-miR-622 prognosis interest in CRB cohort. The prognosis interest of the hsa-miR-622 and other known factors as surgery outcome and stage were assessed using the Cox univariate and multivariate analyses by the sequential method.

| Variable | Description | Univariate | | | Multivariate | | |
|---|---|---|---|---|---|---|---|
| | | HR | CI95% | p-value | HR | CI95% | p-value |
| Progression free survival | | | | | | | |
| hsa-miR-622 | High/Low | 1.11 | [0.5-2.6] | 0.81 | — | — | NS |
| Surgical macroscopic residues | Presence/Absence (R0) | 1.44 | [0.6-3.3] | 0.39 | — | — | NS |
| Stage | IV/III | 1.22 | [0.5-3.1] | 0.68 | — | — | NS |
| Overall survival | | | | | | | |
| hsa-miR-622 | High/Low | 3.43 | [1.3-8.7] | 0.0098 | 2.66 | [1.03-6.9] | 0.044 |
| Surgical macroscopic residues | Presence/Absence (R0) | 3.41 | [1.1-10.2] | 0.028 | — | — | NS |
| Stage | IV/III | 0.87 | [0.3-2.6] | 0.80 | — | — | NS |

HR: Hazard Ratio;
CI95%: Confidence Interval 95%;
NS: Not Significant.

In the CRB cohort, using the cutoff value of 0.280 zmol/μL, the high miR-622 expression group includes 4 of the 7 platinum resistant patients (early relapsers) with 57.1% of sensitivity, 71.4% of specificity, 40.0% of true predictive value and 83.3% of false predictive value.

In the CRB cohort, using the cutoff value of 0.280 zmol/μL, the high miR-622 expression group includes 6 of performed (NACT did not undergo primary surgery). High hsa-miR-622 expression group was significantly associated with PFS (HR=2.82, CI95% 1.3-6.2, p=0.010) and OS (HR=4.00, CI95% 1.1-14.7, p=0.037) in univariate analysis (see Table 3). Additionally, hsa-miR-622 expression was an independent prognostic factor for PFS (p=0.0057) and OS (p=0.036) when analyzed in multivariate analysis adjusting for the clinical covariate.

TABLE 3

Univariate and multivariate analyses of the serum hsa-miR-622 prognosis interest in miRSA cohort. The prognosis interest of the hsa-miR-622 and other known factors as stage were assessed using the Cox univariate and multivariate analyses by the sequential method.

| | | Univariate | | | Multivariate | | |
|---|---|---|---|---|---|---|---|
| Variable | Description | HR | CI95% | p-value | HR | CI95% | p-value |
| Progression free survival | | | | | | | |
| hsa-miR-622 | High/Low | 2.82 | [1.3-6.2] | 0.010 | 3.17 | [1.4-7.2] | 0.0057 |
| Stage | IV/III | 0.61 | [0.3-1.4] | 0.25 | — | — | NS |
| Overall survival | | | | | | | |
| hsa-miR-622 | High/Low | 4.00 | [1.1-14.7] | 0.037 | 4.03 | [1.1-14.8] | 0.036 |
| Stage | IV/III | 0.83 | [0.3-2.7] | 0.76 | — | — | NS |

HR: Hazard Ratio;
CI95%: Confidence Interval 95%;
NS: Not Significant.

In the miRSA cohort, using the cutoff value of 0.124 zmol/μL, the high hsa-miR-622 expression group includes 9 of the 10 platinum resistant patients (early relapsers) with 90.0% of sensitivity, 56.0% of specificity, 45.0% of true predictive value and 93.3% of false predictive value.

In the miRSA cohort, using the cutoff value of 0.124 zmol/μL, the high hsa-miR-622 expression group includes 8 of the 10 short survivors with 80.0% of sensitivity, 60.0% of specificity, 66.7% of true predictive value and 75.0% of false predictive value.

Example III: Association of Serum Hsa-miR-622 Expression Levels and Overall Survival in NACT Patients of CRB Cohort Based on previous observation showing the prognostic interest of a hsa-miR-622 on NACT patients of the miRSA cohort, in a preliminary manner, the same threshold of 0.124 zmol/μL was used on NACT patients from the CRB cohort. Patients were separated in two groups of high and low hsa-miR-622 expression (cutoff=0.124 zmol/u L). Interestingly, it was found that high serum hsa-miR-622 expression group shows worse PFS and OS compared with low hsa-miR-622 expression group (median PFS 20.3 versus 16.8 months, log rank p=0.17 and median OS 35.9 versus 15.1 months, log rank p=0.29) (see FIG. 3).

Example IV: Prognosis Interest of Serum Hsa-miR-622 Expression Levels at Baseline in miRSA Cohort Supplementary analyses were conducted to investigate the prognosis interest of serum hsa-miR-622 expression levels at baseline.

First, the prognosis interest of serum hsa-miR-622 expression levels was evaluated at baseline in miRSA cohort (n=65). Patients were classified according to their PFI in platinum-resistant (<6 months) and platinum-sensitive (>6 months) relapse, and using a ROC curve the optimal cut-off expression was fixed at 77 copies/μL (0-128 zmol/L) (see FIG. 4A). High miR-622 group (n=31, 24 events) was associated with significant lower PFS (median 15-4 versus 24.4 months; log rank p=0-049; HR 1-78 95% CI 1-0-3-2, p=0.052; see FIG. 4B) than low group (n=34, 22 events). High group (12 events) was also associated with significant lower OS (median 29-7 versus 40-6 months; log rank p=0-0046; HR 4-49 95% CI Jan. 4, 2014-0, p=0.0095; see FIG. 4C) than low group (5 events).

Next, univariate and multivariate analyses of miRSA cohort at baseline were performed.

High hsa-miR-622 expression group was significantly associated with lower PFS (HR=1.78, CI95% 1.0-3.2, p=0.052) and OS (HR=4.49, CI95% 1.4-14.0, p=0.0095) in univariate analysis (see Table 4). Additionally, hsa-miR-622 expression was an independent prognostic factor for PFS (p=0.015) and OS (p=0.0011) when analyzed in multivariate analysis adjusting for the clinical covariate.

TABLE 4

Univariate and multivariate analyses of the serum hsa-miR-622 prognosis interest in miRSA cohort at baseline. The prognosis interest of the hsa-miR-622 and other known factors as stage were assessed using the Cox univariate and multivariate analyses by the sequential method.

| Cohorts miRSA Baseline (n = 65) | Survivals | Univariate HR | CI95% | p-value | Multivariate HR | CI95% | p-value |
|---|---|---|---|---|---|---|---|
| | Progression Free Survival | | | | | | |
| hsa-miR-622 | Higher/Lower than 0.128 zmol/µL | 1.78 | [1.0-3.2] | 0.052 | 2.11 | [1.2-3.8] | 0.015 |
| Primary surgery outcome | Suboptimal/Optimal | 2.08 | [1.2-3.7] | 0.014 | 2.42 | [1.3-4.4] | 0.0043 |
| Treatment management | NACT/PDS | 1.91 | [1.1-3.5] | 0.033 | — | — | — |
| | Overall Survival | | | | | | |
| hsa-miR-622 | Higher/Lower than 0.128 zmol/µL | 4.49 | [1.4-14.0] | 0.0095 | 7.68 | [2.2-26.2] | 0.0011 |
| Primary surgery outcome | Suboptimal/Optimal | 3.26 | [1.2-9.2] | 0.024 | 6.3 | [1.9-20.4] | 0.0022 |
| Treatment management | NACT/PDS | 4.45 | [1.3-15.7] | 0.020 | — | — | — |

HR: Hazard Ratio;
CI95%: Confidence Interval 95%;
NS: Not Significant.

Example V: Prognosis Interest of Serum Hsa-miR-622 Expression Levels at Baseline in CRB Cohort The prognosis interest of serum hsa-miR-622 expression levels was also evaluated at baseline in CRB cohort (n=65). Using the same cut-off value, high group (n=52, 42 events) was associated with a significant risk of death (median 30.3 versus 48-9 months; log rank p=0.040; HR 2.28 95% CI 1.0-5-1, p=0.045; see FIG. 4D) than low group (n=13, 7 events).

Next, univariate and multivariate analyses of CRB cohort at baseline were performed. High hsa-miR-622 expression group was significantly associated with lower OS (HR=2.28, CI95% 1.0-5.1, p=0.045) in univariate analysis (see Table 5).

TABLE 5

Univariate and multivariate analyses of the serum hsa-miR-622 prognosis interest in CRB cohort at baseline. The prognosis interest of the hsa-miR-622 and other known factors as stage were assessed using the Cox univariate and multivariate analyses by the sequential method.

| Cohorts CRB Baseline (n = 65) | Survivals Overall Survival | Univariate HR | CI95% | p-value | Multivariate HR | CI95% | p-value |
|---|---|---|---|---|---|---|---|
| hsa-miR-622 | Higher/Lower than 0.128 zmol/µL | 2.28 | [1.0-5.1] | 0.045 | 1.87 | [0.8-4.3] | 0.14 |
| Primary surgery outcome | Suboptimal/Optimal | 1.93 | [1.1-3.4] | 0.025 | 1.69 | [0.9-3.1] | 0.081 |
| Treatment management | NACT/PDS | 2.96 | [1.1-7.7] | 0.027 | — | — | — |

HR: Hazard Ratio;
CI95%: Confidence Interval 95%;
NS: Not Significant.

Example VI: Prognosis Interest of Serum Hsa-miR-622 Expression Levels at Relapse in CRB Cohort Then, the kinetic prognosis interest of serum hsa-miR-622 expression levels was investigated at relapse in CRB (n=35). Patients were classed into short (<12 months) and long (≥12 months) survivors according to the residual OS. The optimal cut-off expression was fixed at 205 copies/μL (0.34 zmol/μL) using a ROC curve (see FIG. 5A). High miR 622 group (n=11, 11 events) presents a significant lower OS (median 7.9 versus 20.6 months; log rank p=0.00077; HR 3·56 95% CI 1.6-7.8, p=0·0015; see FIG. 5B) than low group (n=24, 21 events).

Next, univariate and multivariate analyses of CRB cohort at relapse were performed. High hsa-miR-622 expression group was significantly associated with lower OS (HR=3.56, CI95% 1.6-7.8, p=0.0015) in univariate analysis (see Table 6). Additionally, hsa-miR-622 expression was an independent prognostic factor for OS (p=0.0062) when analyzed in multivariate analysis adjusting for the clinical covariate.

TABLE 6

Univariate and multivariate analyses of the serum hsa-miR-622 prognosis interest in CRB cohort at relapse. The prognosis interest of the hsa-miR-622 and other known factors as stage were assessed using the Cox univariate and multivariate analyses by the sequential method.

| Cohorts CRB Relapse (n = 35) | Survivals Overall Survival | Univariate HR | CI95% | p | Multivariate HR | CI95% | p |
|---|---|---|---|---|---|---|---|
| hsa-miR-622 | Higher/Lower than 0.34 zmol/μL | 3.56 | [1.6-7.8] | 0.0015 | 3.15 | [1.4-7.2] | 0.0062 |
| Primary surgery outcome | Suboptimal/Optimal | 3.35 | [1.6-7.1] | 0.0018 | 3.04 | [1.4-6.7] | 0.0059 |
| Relapse | Before/After 6 months | 2.31 | [1.0-5.4] | 0.053 | — | — | — |

HR: Hazard Ratio;
CI95%: Confidence Interval 95%;
NS: Not Significant.

Example VII: Prognosis Interest of Serum Hsa-miR-622 Expression Levels at Relapse in PARPi Eligible Patients from CRB Cohort Moreover, according to second-line PARPi maintenance eligibility criteria, focusing on platinum sensitive patients who respond to second line platinum-based chemotherapy (see FIG. 5C), high miR-622 group (n=2, 2 events) was associated with lower OS (median 15.3 versus 34.8 months; log rank p=0.0026) than low group (n=11, 8 events). Consistently at baseline on the CRB cohort (n=65) using the same cut-off value, high miR-622 group (n=20, 19 events) presents a significant lower OS (median 22.8 versus 35.9 months; log rank p=0.017; HR 2.01 95% CI 1.1-3-6, p=0-019) than the low group (n=45, 30 events).

Example VIII: Prognosis Interest of Serum Hsa-miR-622 Expression Levels Prior to First-Line Chemotherapy in Patients Treated by PARPi Maintenance at Progression The predictive interest of miR-622 was assessed prior to first-line chemotherapy on serum samples from 8 patients treated by PARPi maintenance at progression (CRB cohort). Using the same cut-off values as previously, high miR-622 group (n=2, 1 event) was associated with a significant lower overall survival (OS) (median 34.7 versus 94.9 months; log rank p=0.28; HR 4.24 p=0.31; see FIG. 6) than low miR-622 group (n=6, 3 events).

The invention claimed is:

1. A method for treating an advanced stage III to IV HGSOC patient in relapse comprising:
    administering a conventional platinum-based chemotherapy treatment and/or a PARP inhibitor (PARPi)-based treatment to the HGSOC patient,
    wherein the patient has been identified at relapse as sensitive to the conventional platinum-based chemotherapy treatment and/or the PARP inhibitor (PARPi)-based treatment by a method comprising the steps of:
    (a) obtaining a liquid biological sample from the HGSOC patient at relapse;
    (b) determining at least the concentration of hsa-miR-622 in the liquid biological sample obtained from said HGSOC patient at relapse;
    (c) comparing the determined hsa-miR-622 concentration with at least one reference value at relapse,
    wherein a determined hsa-miR-622 concentration of lower than 0.34 zmol/µl, identifies the patient as a PARPi-sensitive and/or platinum-sensitive patient.

2. The method according to claim 1, wherein the concentration of hsa-miR-622 is determined using RT-qPCR, a microarray or next generation sequencing.

3. The method according to claim 1, wherein said liquid biological sample is selected from the group consisting of urine, blood, serum, plasma, and ascites.

4. The method according to claim 3, wherein the concentration of hsa-miR-622 is determined by assaying the hsa-miR-622 amount in the sample by comparison with miRNAs standard curves obtained by measurement of known amount of synthetic hsa-miR-622 oligonucleotides and by using an exogenous normalization based on the addition of known quantities of cel-miR-39-3p, cel-miR-54-3p, and cel-miR-238-3p in the liquid biological sample just before extracting RNA from the liquid biological sample.

* * * * *

SEQUENCE LISTING

<160> NUMBER OF SEQ ID NOS: 4

<210> SEQ ID NO 1
<211> LENGTH: 21
<212> TYPE: RNA
<213> ORGANISM: Homo sapiens

```
<400> SEQUENCE: 1
acagucugcu gagguuggag c                                              21

<210> SEQ ID NO 2
<211> LENGTH: 96
<212> TYPE: RNA
<213> ORGANISM: Homo sapiens

<400> SEQUENCE: 2
agagaagcug gacaaguacu ggucucagca gauugaggag agcaccacag uggucaucac    60
acagucugcu gagguuggag cugcugagau gacacu                              96

<210> SEQ ID NO 3
<211> LENGTH: 24
<212> TYPE: RNA
<213> ORGANISM: Caenorhabditis elegans

<400> SEQUENCE: 3
uacccguaau cuucauaauc cgag                                           24

<210> SEQ ID NO 4
<211> LENGTH: 23
<212> TYPE: RNA
<213> ORGANISM: Caenorhabditis elegans

<400> SEQUENCE: 4
uuuguacucc gaugccauuc aga                                            23
```